United States Patent
Chen et al.

(10) Patent No.: US 9,777,125 B2
(45) Date of Patent: Oct. 3, 2017

(54) METHOD FOR PRODUCING POLYMER LATEX PARTICLE COATED WITH SILVER NANOPARTICLES

(71) Applicant: NERD SKINCARE INC., San Francisco, CA (US)

(72) Inventors: Ying-Tung Chen, San Francisco, CA (US); Chia-Fen Lee, Tainan (TW); Yu-Syuan Chang, Changhua County (TW); Kuen-Lin Leu, Chiayi County (TW)

(73) Assignees: Nerd Skincare Inc., San Francisco, CA (US); Chia-Fen Lee, Tainan (TW)

( * ) Notice: Subject to any disclaimer, the term of this patent is extended or adjusted under 35 U.S.C. 154(b) by 0 days.

(21) Appl. No.: 14/953,196

(22) Filed: Nov. 27, 2015

(65) Prior Publication Data
US 2017/0114191 A1  Apr. 27, 2017

(30) Foreign Application Priority Data
Oct. 27, 2015 (TW) .............................. 104135206 A

(51) Int. Cl.
| | |
|---|---|
| *C08J 3/215* | (2006.01) |
| *A01N 25/26* | (2006.01) |
| *A01N 59/16* | (2006.01) |
| *A61K 8/02* | (2006.01) |
| *A61K 8/19* | (2006.01) |

(Continued)

(52) U.S. Cl.
CPC .............. *C08J 3/215* (2013.01); *A01N 25/26* (2013.01); *A01N 59/16* (2013.01); *A61K 8/0275* (2013.01); *A61K 8/19* (2013.01); *A61K 8/72* (2013.01); *A61K 9/1629* (2013.01); *A61K 9/1682* (2013.01); *A61K 33/38* (2013.01); *A61K 2800/413* (2013.01); *A61K 2800/56* (2013.01); *A61K 2800/621* (2013.01); *A61K 2800/654* (2013.01); *A61K 2800/805* (2013.01); *C08J 2321/02* (2013.01); *C08J 2325/06* (2013.01)

(58) Field of Classification Search
CPC ........................................................ B01J 13/22
USPC ...................................................... 252/408.1
See application file for complete search history.

(56) References Cited

U.S. PATENT DOCUMENTS 5,552,086 A * 9/1996 Siiman ............. A61K 47/48861
                                                                252/408.1

FOREIGN PATENT DOCUMENTS

| TW | I455718 | 10/2014 |
|---|---|---|
| TW | I455778 | 10/2014 |
| TW | I495481 | 8/2015 |

OTHER PUBLICATIONS

Mpenyana-Monyatsi et al., Cost-Effective Filter Materials Coated with Silver Nanoparticles for the Removal of Pathogenic Bacteria in Groundwater, 2012, International Journal of Environemental Research and Public Health, vol. 9, pp. 244-271.*

* cited by examiner

*Primary Examiner* — Dah-Wei D Yuan
*Assistant Examiner* — Andrew Bowman
(74) *Attorney, Agent, or Firm* — Rosenberg, Klein & Lee

(57) ABSTRACT

This invention is related to a method for producing polymer latex particle coated with silver nanoparticles. First, a polymer latex particle suspension is mixed with a silver nitrate solution in a weight ratio of 10:1 to 1:10 at 50° C. to 90° C. for 10 to 120 minutes to form a mixed solution. After the temperature of the mix solution is cooled to 50° C. to 85° C., a sodium citrate solution is added to react with the mixed solution for 10 to 240 minutes to form a polymer latex (Continued)

particle coated with silver nanoparticles, which has antibacterial activity.

6 Claims, 7 Drawing Sheets

(51) Int. Cl.
*A61K 8/72* (2006.01)
*A61K 9/16* (2006.01)
*A61K 33/38* (2006.01)

METHOD FOR PRODUCING POLYMER LATEX PARTICLE COATED WITH SILVER NANOPARTICLES

BACKGROUND OF THE INVENTION

Field of the Invention

The present invention relates to a method for producing polymer latex particle coated with silver nanoparticles. More particularly, the method is for firmly and evenly coating the silver nanoparticles onto the surface of the polymer latex particle in a specific production condition, therefore, the obtained latex particle of the present invention has well antibacterial activity, which not only is substituted to the preservative in the cosmetics, but also resolves the problem that the silver nanoparticles go into the human cells by skin, and the silver particles are dispersed in nanoscale to increase its antibacterial activity.

Description of Related Art

Recently, the cosmetics have become indispensable daily necessaries for people who love beauty. In order to elongate the effective period of the cosmetics, the chemical antibacterial agent or preservative is added into the cosmetics to extend shelf life of the cosmetics. The preservative in common use is organic chemicals such as Paraben, Phenoxyethanol, Benzoic acid, or Sorbic acid, which has good antibacterial activity. However, when long-term use of the organic chemical preservative to cause the overdose accumulation, there still has doubt that the organic chemical preservative causes the skin allergies and has toxicity.

Besides the chemical synthesized organic antibacterial agent or preservative, the well-known inorganic antibacterial agent is silver nanoparticle, which has extremely good deodorant activity and antibacterial activity and is high temperature resistant. In addition, the silver nanoparticle avoids the problem that it needs to contact ultraviolet when use a titanium dioxide photocatalyst. Accordingly, many inventions disclose that the nanoparticle is combined with different base material to make the base material having additional antibacterial activity.

For example, the TW Patent application with the Issued No. 1455778 B, "producing method for combining metal nanoparticle to the surface of base material", comprises the following steps. A default base material is immersed into a saline solution containing metal ions with default concentration, making the metal ions attach to the base material. Then, the base material is moved out, and a reaction solution containing a default reduction solution is added onto the base material to provide energy for reducing the metal ions, which are attached on the surface of the base material, to the metal nanoparticle. Finally, the base material is dried by a default method to obtain a base material which is combined with metal nanoparticle. Accordingly, the product is not easy to remain with the harmful chemicals, so the product does not need to be processed by the complicated process. The TW Patent application with the Issued No. 1495481 B, "polysiloxane composite particle, method for making the same, and cosmetics", discloses a polysiloxane composite particle, which can be added into the deodorant cosmetics. It is characterized that 100 mass parts of polysiloxane elastomer globule is coated with 0.5 to 25 mass parts of polysiloxane resin, wherein the polysiloxane elastomer globule has a mean diameter of 0.1 to 100 μm, and the main constituent of the polysiloxane resin is silsesquioxane and the polysiloxane resin contains inorganic micro particle with a mean diameter below 100 nm. And the TW Patent application with the Issued No. 1455718, "a composite of silver nanoparticles and clay for antibacterial growth and the making method of the same", discloses a composite of silver nanoparticles and clay for applying to biological, medical, chemical, chemical industry, or material area (for example, antibacterial growth or medical treatment for burns and scalds). The composite is a power, comprising a metal particle and layered inorganic clay, wherein the layered inorganic clay has an aspect ratio of about 100 to 1,000 and is as the carrier of the metal particle, making the metal particle disperse in nanoscale. The composite of silver nanoparticles and clay for antibacterial growth has a size of about 5 nm to 100 nm. The layered inorganic clay can be bentonite or nanosilicate platelet. When the layered inorganic clay is bentonite, the metal nanoparticle/clay weight ratio is 1/100 to 1/13.83 or 1/6.944 to 100/1. When the layered inorganic clay is nanosilicate platelet, the metal nanoparticle/clay weight ratio is 1/13.43 to 100/1. The metal is silver.

According to the literature, although there has many application for silver nanoparticle combined with different base material, how to uniformly combine the silver nanoparticle to the base material is determined by different making method. Therefore, how to invent the best polystyrene latex particle coated with silver nanoparticles as antibacterial agent is the breakthrough direction for inventors in the related area.

SUMMARY OF THE INVENTION

Therefore, the object of the present invention is related to a method for producing polymer latex particle coated with silver nanoparticles, which is a method is for firmly and evenly coating the silver nanoparticles onto the surface of the polymer latex particle. Therefore, the latex particle obtained by the producing method of the present invention has well antibacterial activity to be a preservative in the cosmetics.

For the above object, a method for producing polymer latex particle coated with silver nanoparticles comprises the steps described below. First, a polymer latex particle suspension is mixed with a silver nitrate ($AgNO_3$) solution in a weight ratio of 10:1 to 1:10 at 50° C. to 90° C. for 10 to 120 minutes to form a mixed solution. After the temperature of the mixed solution is cooled to 50° C. to 85° C., a sodium citrate solution is added to react with the mixed solution for 10 to 240 minutes (the better is for 20 to 130 minutes) to form a polymer latex particle coated with silver nanoparticles, wherein the polymer latex particle has a diameter greater than 50 nm, and the silver nanoparticle has a diameter of 1 to 500 nm.

According to an example of the present invention, the polymer latex particle suspension contains 3.85 wt % polymer latex particles in water.

According to an embodiment of the present invention, the polymer latex particle is polystyrene latex particle, poly(methyl methacrylate) latex particle, poly(butyl acrylate) latex particle, poly(styrene-methyl methacrylate) copolymer latex particle, poly(styrene-butyl acrylate) copolymer latex particle, or poly(methyl methacrylate-butyl acrylate) copolymer latex particle. In an example, the polymer latex particle is polystyrene latex particle and the method for preparing the polystyrene latex particle comprises the step as described below. First, styrene, polyetherimide (PEI), and methanol are mixed into de-ionized water and heated to 50° C. to 90° C. to form a mixture. Then, an initiator azobisisobutyronitrile (AIBN) is added to react with the mixture for 3 to 12 hours. Finally, the purified polystyrene latex particle is obtained by centrifuge.

According to an example of the present invention, the silver nitrate solution contains 1.96 wt % silver nitrate in water and the sodium citrate solution contains 16.2 wt % sodium citrate in water.

According to an example of the present invention, the polymer latex particle coated with silver nanoparticle is used for inhibiting the growth of gram positive bacteria, gram negative bacteria and fungi.

According to an example of the present invention, the polymer latex particle coated with silver nanoparticle is used in the cosmetic composition or medical composition to be a bacteriostatic agent or a preservative.

DETAILED DESCRIPTION OF THE PREFERRED EMBODIMENT

Figure 1:
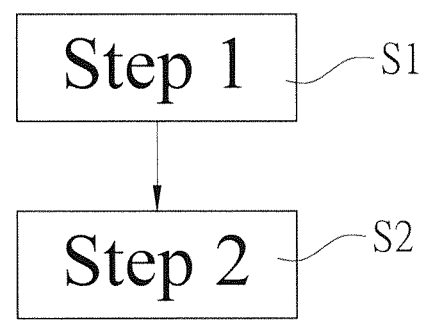
FIG. 1 is a flow chart of a method for producing polystyrene latex particle coated with silver nanoparticles according to an embodiment of the present invention.

Please refer to FIG. 1, which is a flow chart of a method for producing polystyrene latex particle coated with silver nanoparticles according to an embodiment of the present invention.

Step 1 (S1): A polymer latex particle suspension is mixed with a silver nitrate ($AgNO_3$) solution in a weight ratio of 10:1 to 1:10 at 50° C. to 90° C. for 10 to 120 minutes to form a mixed solution. According to an example, the polymer latex particle suspension contains 3.85 wt % polymer latex particles in water, the silver nitrate solution contains 1.96 wt % silver nitrate in water, and the sodium citrate solution contains 16.2 wt % sodium citrate in water.

Step 2 (S2): After the temperature of the mixed solution is cooled to 50° C. to 85° C., a sodium citrate solution is added to react with the mixed solution for 10 to 240 minutes (the better is for 20 to 130 minutes) to form a polymer latex particle coated with silver nanoparticles, which has the activity for inhibiting the growth of gram positive bacteria, gram negative bacteria and fungi. Therefore, the polymer latex particle coated with silver nanoparticles obtained by the present invention is added in cosmetic composition or medical composition to be a preservative. In an example of the present invention, the polymer latex particle has a diameter greater than 50 nm, and the silver nanoparticle has a diameter of 1 to 500 nm.

The foregoing polymer latex particle is polystyrene latex particle, poly(methyl methacrylate) latex particle, poly(butyl acrylate) latex particle, poly(styrene-methyl methacrylate) copolymer latex particle, poly(styrene-butyl acrylate) copolymer latex particle, or poly(methyl methacrylate-butyl acrylate) copolymer latex particle. According to an example, the polymer latex particle is polystyrene latex particle and the method for preparing the polystyrene latex particle is described below. First, styrene, polyetherimide (PEI), and methanol are mixed in de-ionized water and heated to 50° C. to 90° C. to form a mixture. Then, an initiator azobisisobutyronitrile (AIBN) is added to react with the mixture for 3 to 12 hours. Finally, the purified polystyrene latex particle is obtained by centrifuge.

The method for producing polymer latex particle coated with silver nanoparticles of the present invention could be performed by the following examples to further show the range of the actual application, but not to limit the spirit of the present invention.

Example 1 Prepare Polystyrene Latex Particle

The method for preparing the polystyrene latex particle is described below. First, 1.9 g polyetherimide (PEI) and 30 g methanol are mixed in 1 g de-ionized water and put into a reactor (using low speed agitation). Second, 0.3 g AIBN (azobisisobutyronitrile) is dissolved in 15 g methanol to form an ABIN-methanol solution. Third, 10 g styrene is added into the reactor to mix with the solution in first step, and the reaction solution is heated to 70° C. for 15 minutes to form a mixture. Then, the ABIN-methanol solution prepared in second step is quickly added into the reactor to react with the mixture for 8 hours at 70° C. to form a PS (polystyrene) latex emulsion. Finally, the purified polystyrene (PS) latex particle is obtained by centrifuge, which the polystyrene latex particle has a mean diameter greater than 100 nm (about 100 to 2000 nm).

Example 2

Figure 2:
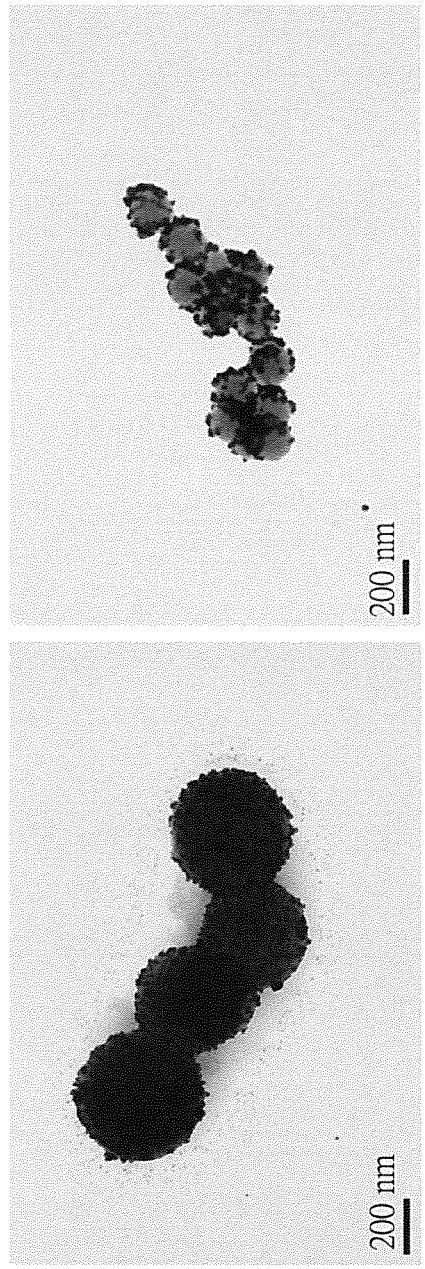
FIG. 2 is a microscopic photograph of a polystyrene latex particle coated with silver nanoparticles obtained by an example of the present invention.

Please refer to Table 1. In this example, the method for producing polystyrene latex particle containing silver nanoparticle is described below. First, 1 g polystyrene (PS) latex particle prepared by the example 1 is mixed with 25 g di-ionized water to form a polystyrene latex particle suspension. Second, the polystyrene latex particle suspension is put into a reactor without condenser and heated to 90° C. as well as agitated continuously by feeding nitrogen. Third, 0.1 g silver nitrate ($AgNO_3$) is mixed with 5 g di-ionized water to form a silver nitrate solution. Then, the silver nitrate solution is added into the reactor at 90° C. (at this time the color of the solution in the reactor is gradually changed to light yellow) to react with the polystyrene latex particle suspension for 1 hour to form a mixed solution. Finally, after the temperature of the mixed solution is cooled to 85° C., a sodium citrate solution (1.94 g sodium citrate dissolved in 10 g di-ionized water) is added to react with the mixed solution for 10 minutes and the color of the mixed solution is gradually changed to black to obtain a polystyrene latex particle coated with silver nanoparticles. The polystyrene latex particle has a mean diameter of 390 to 990 nm, and the silver nanoparticle has a mean diameter of 5 to 100 nm. Please refer to FIG. 2, which shows a microscopic photograph of the polystyrene latex particle coated with silver nanoparticles obtained by this example observed by a transmission Electron Microscopy (TEM). The reaction time of the sodium citrate with the mixed solution is only 10 minutes, which time is too short, so the amount of the synthetic silver nanoparticles is too little and there is not enough time for the silver nanoparticles to coat onto the PS latex particle. Therefore, the silver nanoparticles cannot be coated all the surface of the PS latex particle, resulting that the surface of some PS latex particles is uncovered.

TABLE 1

| Material | Feeding amount (g) |
| --- | --- |
| PS latex particle | 1 |
| silver nitrate | 0.1 |
| sodium citrate | 1.94 |
| di-ionized water | 40 |

Example 3

Figure 3:
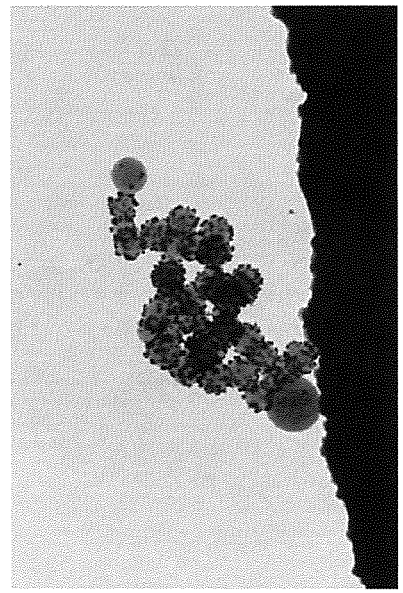
FIG. 3 is a microscopic photograph of a polystyrene latex particle coated with silver nanoparticles obtained by another example of the present invention.
Figure 3:
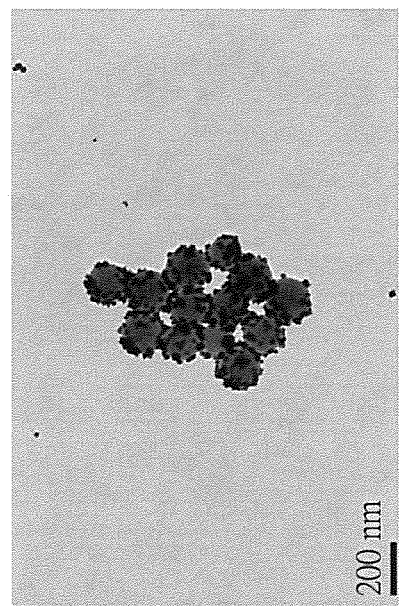

Please refer to Table 2. In this example, the method for producing polystyrene latex particle coated with silver nanoparticles is described below. First, 1 g polystyrene (PS) latex particle prepared by the example 1 is mixed with 25 g di-ionized water to form a polystyrene latex particle suspension. Second, the polystyrene latex particle suspension is put into a reactor without condenser and heated to 90° C. to 95° C. as well as agitated continuously by feeding nitrogen. Third, 0.1 g silver nitrate ($AgNO_3$) is mixed with 5 g di-ionized water to form a silver nitrate solution. Then, the silver nitrate solution is added into the reactor at 90° C. to 95° C. (at this time the color of the solution in the reactor is gradually changed to light yellow) to react with the polystyrene latex particle suspension for 1 hour to form a mixed solution. Finally, after the temperature of the mixed solution is cooled to 80° C., a sodium citrate solution (1.94 g sodium citrate dissolved in 10 g di-ionized water) is added to react with the mixed solution for 20 minutes and the color of the mixed solution is gradually changed to black to obtain a polystyrene latex particle coated with silver nanoparticles. The polystyrene latex particle has a mean diameter of 390 to 990 nm, and the silver nanoparticle has a mean diameter of 5 to 100 nm. Please refer to FIG. 3, which shows a microscopic photograph of a polystyrene latex particle coated with silver nanoparticles obtained by this example observed by a transmission Electron Microscopy (TEM). The reaction time of the sodium citrate with the mixed solution is only 20 minutes, which time is too short, so the amount of the synthetic silver nanoparticles is too little. On the other hand, the reaction temperature is too high, resulting in synthesizing the synthetic silver nanoparticles too quickly, so there is not enough time for the silver nanoparticles to coat onto the PS latex particle. Therefore, the silver nanoparticles cannot be coated all the surface of the PS latex particle, resulting that the surface of some PS latex particles is uncovered. If the reaction time of the sodium citrate with the mixed solution is further extended to 30 minutes, the result is similar to the foregoing. Accordingly, it needs to test the different condition.

TABLE 2

| Material | Feeding amount (g) |
| --- | --- |
| PS latex particle | 1 |
| silver nitrate | 0.1 |
| sodium citrate | 1.94 |
| di-ionized water | 40 |

Example 4

Figure 4:
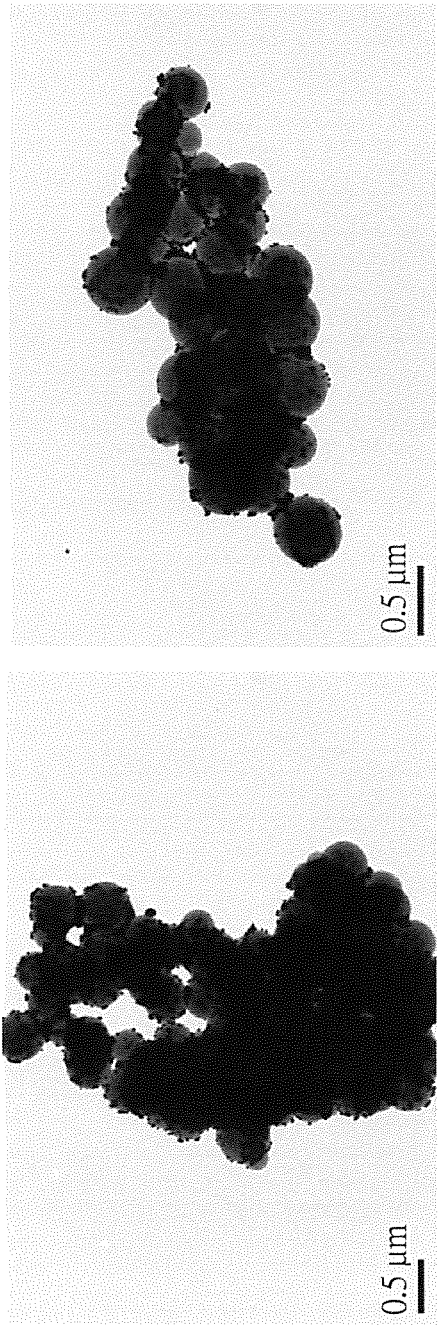
FIG. 4 is a microscopic photograph of a polystyrene latex particle coated with silver nanoparticles obtained by another example of the present invention.

Please refer to Table 3. In this example, the method for producing polystyrene latex particle coated with silver nanoparticles is described below. First, 1 g polystyrene (PS) latex particle prepared by the example 1 is mixed with 25 g di-ionized water to form a polystyrene latex particle suspension. Second, the polystyrene latex particle suspension is put into a reactor without condenser and heated to 90° C. as well as agitated continuously by feeding nitrogen. Third, 0.3 g silver nitrate ($AgNO_3$) is mixed with 15 g di-ionized water to form a silver nitrate solution. Then, the silver nitrate solution is added into the reactor at 90° C. (at this time the color of the solution in the reactor is gradually changed to light yellow) to react with the polystyrene latex particle suspension for 1.5 hour to form a mixed solution. Finally, after the temperature of the mixed solution is cooled to 80° C., a sodium citrate solution (5.82 g sodium citrate dissolved in 30 g di-ionized water) is added to react with the mixed solution for 30 minutes and the color of the mixed solution is gradually changed to black to obtain a polystyrene latex particle coated with silver nanoparticles. Please refer to FIG. 4, which shows a microscopic photograph of a polystyrene latex particle coated with silver nanoparticles obtained by this example observed by a transmission Electron Microscopy (TEM). As the amounts of the silver nitrate and the sodium citrate are added too much and the reaction time of the sodium citrate with the mixed solution is 1.5 hours, which time is longer, the silver nanoparticles are produced too much, resulting in aggregation of the silver nanoparticles.

TABLE 3

| Material | Feeding amount (g) |
| --- | --- |
| PS latex particle | 1 |
| silver nitrate | 0.3 |
| sodium citrate | 5.82 |
| di-ionized water | 70 |

Example 5

Figure 5:
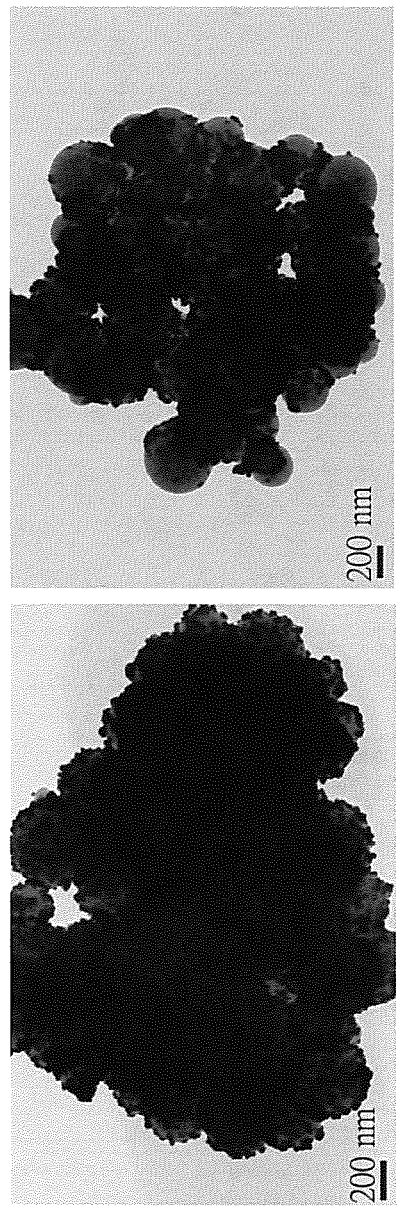
FIG. 5 is a microscopic photograph of a polystyrene latex particle coated with silver nanoparticles obtained by another example of the present invention.

Please refer to Table 4. In this example, the method for producing polystyrene latex particle coated with silver nanoparticles is described below. First, 1 g polystyrene (PS) latex particle prepared by the example 1 is mixed with 25 g di-ionized water to form a polystyrene latex particle suspension. Second, the polystyrene latex particle suspension is put into a reactor without condenser and heated to 90° C. as well as agitated continuously by feeding nitrogen. Third, 0.3 g silver nitrate ($AgNO_3$) is mixed with 15 g di-ionized water to form a silver nitrate solution. Then, the silver nitrate solution is added into the reactor at 90° C. (at this time the color of the solution in the reactor is gradually changed to light yellow) to react with the polystyrene latex particle suspension for 1 hour to form a mixed solution. Finally, after the temperature of the mixed solution is cooled to 80° C., a sodium citrate solution (5.82 g sodium citrate dissolved in 30 g di-ionized water) is added to react with the mixed solution for 30 minutes and the color of the mixed solution is gradually changed to black to obtain a polystyrene latex particle coated with silver nanoparticles. Please refer to FIG. 5, which shows a microscopic photograph of a polystyrene latex particle coated with silver nanoparticles obtained by this example observed by a transmission Electron Microscopy (TEM). As the amounts of the silver nitrate and the sodium citrate are added too much, the silver nanoparticles are produced too much, resulting in aggregation of the silver nanoparticles.

TABLE 4

| Material | Feeding amount (g) |
|---|---|
| PS latex particle | 1 |
| silver nitrate | 0.3 |
| sodium citrate | 5.82 |
| di-ionized water | 70 |

Example 6

Figure 6:
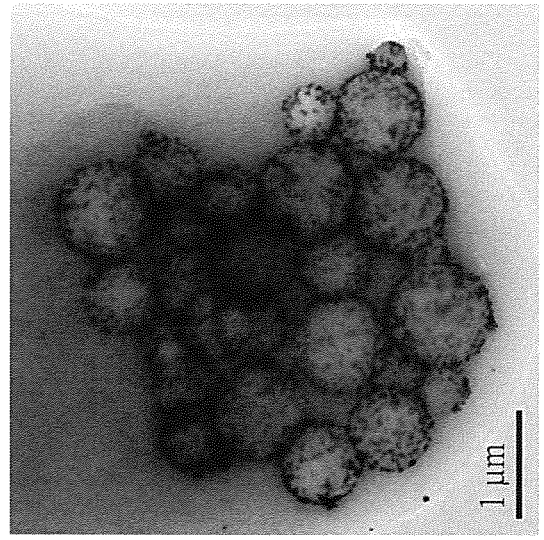
FIG. 6 is a microscopic photograph of a polystyrene latex particle coated with silver nanoparticles obtained by the other example of the present invention.
Figure 6:
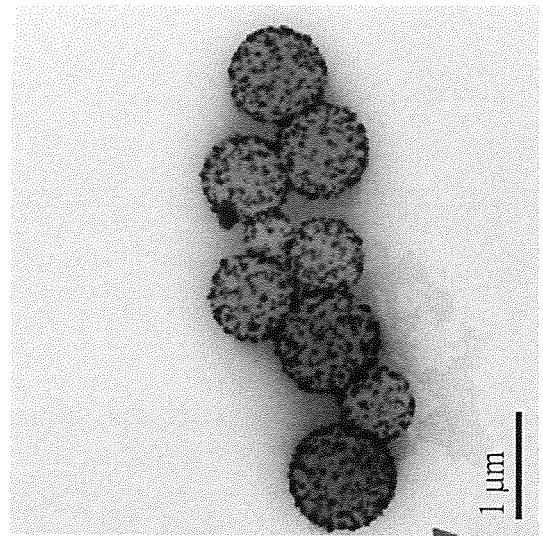

Please refer to Table 5. In this example, the method for producing polystyrene latex particle coated with silver nanoparticles is described below. First, 1 g polystyrene (PS) latex particle prepared by the example 1 is mixed with 25 g di-ionized water to form a polystyrene latex particle suspension. Second, the polystyrene latex particle suspension is put into a reactor without condenser and heated to 90° C. as well as agitated continuously by feeding nitrogen. Third, 0.1 g silver nitrate ($AgNO_3$) is mixed with 5 g di-ionized water to form a silver nitrate solution. Then, the silver nitrate solution is added into the reactor at 95° C. (at this time the color of the solution in the reactor is gradually changed to light yellow) to react with the polystyrene latex particle suspension for 1 hour to form a mixed solution. Finally, after the temperature of the mixed solution is cooled to 85° C., a sodium citrate solution (1.94 g sodium citrate dissolved in 10 g di-ionized water) is added to react with the mixed solution for 30 minutes and the color of the mixed solution is gradually changed to black to obtain a polystyrene latex particle coated with silver nanoparticles. The polystyrene latex particle has a mean diameter of 390 to 990 nm, and the silver nanoparticle has a mean diameter of 5 to 100 nm. Please refer to FIG. 6, which shows a microscopic photograph of a polystyrene latex particle coated with silver nanoparticles obtained by this example observed by a transmission Electron Microscopy (TEM). The appropriate amount of the silver nitrate is added and the reaction time is appropriate, so the amount of the synthesized silver nanoparticles is proper. Furthermore, the reaction time is longer, so there is enough time for the silver nanoparticles to coat onto the PS latex particle, making the surface of the PS latex particle being uniformly coated with the silver nanoparticles.

TABLE 5

| Material | Feeding amount (g) |
|---|---|
| PS latex particle | 1 |
| silver nitrate | 0.1 |
| sodium citrate | 1.94 |
| di-ionized water | 40 |

Example 7 Minimum Inhibitory Concentration (MIC) Test

The minimum inhibitory concentration (MIC) of the polystyrene latex particle coated with the silver nanoparticles obtained in sample 6 is tested. The minimum inhibitory concentration is the lowest concentration of a sample that will inhibit the growth of a microorganism over 90%. The MIC of the sample is lower, the bacteriostatic activity of the sample is better. In this example, the growth of *Staphylococcus aureus* (gram positive bacteria) and *Escherichia coli* (gram negative bacteria) is tested. The antibacterial samples (the polystyrene latex particle coated with the silver nanoparticles) are added into the sterile tubes at different concentration (0-0.02%), respectively. Next, 1 c.c nutrient broth or TSB broth is added and mixed with the incubation broth containing the known bacteria. Then, the mixture is incubated in an incubator at 37° C. for 1 day. After incubation, the clear suspension is continuously diluted by 10 fold and then the dilution is spread on the agar to incubate under a proper condition. After incubation, the amount of colony is counted to determine the MIC.

Figure 7:
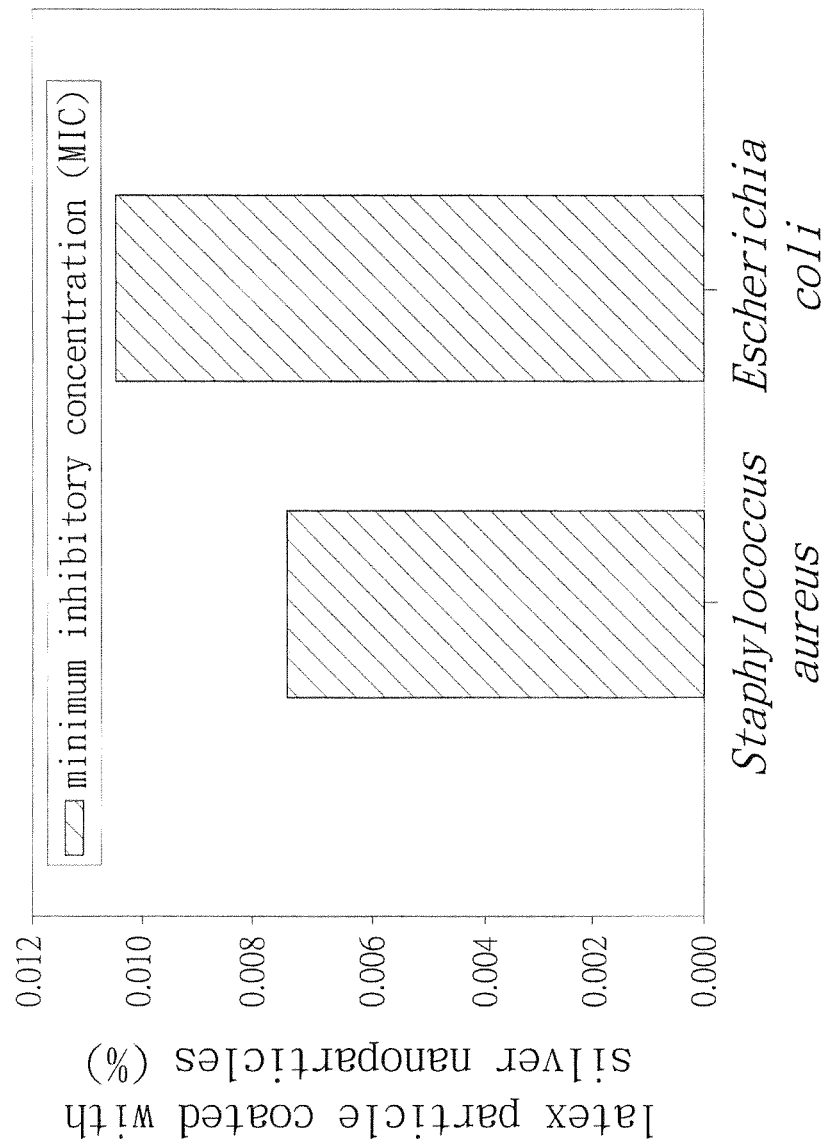
FIG. 7 is the result of minimum inhibitory concentration test of a polystyrene latex particle coated with silver nanoparticles obtained by the present invention.

The result is shown in FIG. 7. The polystyrene latex particle coated with the silver nanoparticles obtained in sample 6 has the bacteriostatic activity. The minimum inhibitory concentration of the polystyrene latex particle coated with the silver nanoparticles is 0.0075% for *Staphylococcus aureus* and 0.011% for *Escherichia coli*.

As the surface of the polystyrene latex particle of the present invention is coated uniformly with the silver nanoparticles, the polystyrene latex particle of the present invention has well antibacterial activity. Furthermore, the silver nanoparticles are firmly coated on the surface of the polystyrene latex particle without separation. Therefore, the polystyrene latex particle coated with silver nanoparticles obtained by the present invention not only is substituted to the preservative in the cosmetics, but also resolves the problem that the silver nanoparticles go into the human cells by skin, and the silver particles are dispersed in nanoscale to increase its antibacterial activity.

What is claimed is:

1. A method for producing polymer latex particle coated with silver nanoparticles, comprising the step of:
   mixing a polymer latex particle suspension with a silver nitrate ($AgNO_3$) solution in a weight ratio of 10:1 to 1:10 at 50° C. to 90° C. for 10 to 120 minutes to form a mixed solution; and
   cooling the temperature of the mixed solution to 50° C. to 85° C. and then adding a sodium citrate solution to react with the mixed solution for 10 to 240 minutes to form a polymer latex particle coated with silver nanoparticles, wherein the polymer latex particle has a diameter greater than 50 nm, and the silver nanoparticle has a diameter of 1 to 500 nm;
   wherein the polymer latex particle is a polystyrene latex particle and the method for preparing the polystyrene latex particle comprises the step of:
   mixing styrene, polyetherimide (PEI), and methanol in de-ionized water and heating to 50° C. to 90° C. to form a mixture;
   adding an initiator azobisisobutyronitrile (AIBN) to react with the mixture for 3 to 12 hours; and
   obtaining the purified polystyrene latex particle by centrifuge.

2. The method for producing polymer latex particle coated with silver nanoparticles as claim 1, wherein the polymer latex particle suspension contains 3.85 wt % polymer latex particles in water.

3. The method for producing polymer latex particle coated with silver nanoparticles as claim 1, wherein the silver nitrate solution contains 1.96 wt % silver nitrate in water and the sodium citrate solution contains 16.2 wt % sodium citrate in water.

4. The method for producing polymer latex particle coated with silver nanoparticles as claim 1, wherein the step of reacting with the mixed solution is for 20 to 130 minutes.

5. The method for producing polymer latex particle coated with silver nanoparticles as claim 1, wherein the polymer latex particle coated with silver nanoparticles is used for inhibiting the growth of gram positive bacteria, gram negative bacteria and fungi.

6. The method for producing polymer latex particle coated with silver nanoparticles as claim 1, wherein the polymer latex particle coated with silver nanoparticles is used in cosmetic composition or medical composition.

* * * * *